United States Patent [19]
Ahn

[11] Patent Number: 5,538,735
[45] Date of Patent: Jul. 23, 1996

[54] METHOD OF MAKING A DRUG DELIVERY SYSTEM USING HOLLOW FIBERS

[76] Inventor: Sam S. Ahn, 724 Warner Ave., Los Angeles, Calif. 90024

[21] Appl. No.: 19,884

[22] Filed: Feb. 19, 1993

[51] Int. Cl.$^6$ .............................. A61K 9/70; D01F 11/00; D01F 11/02; D01F 11/06
[52] U.S. Cl. ............................................ 424/443; 428/396
[58] Field of Search ........................... 424/443; 428/396, 428/320.2, 321.1, 311.5, 311.7

[56] References Cited

U.S. PATENT DOCUMENTS

| | | | |
|---|---|---|---|
| 3,745,061 | 6/1973 | Champaneria et al. | 161/78 |
| 3,772,137 | 11/1973 | Tolliver | 161/169 |
| 3,875,008 | 4/1975 | Yoshino et al. | 435/182 |
| 4,801,458 | 1/1989 | Hidaka et al. | 424/443 |
| 4,833,172 | 5/1989 | Schwarz et al. | 521/62 |
| 4,836,763 | 6/1989 | Broaddus | 425/131.5 |
| 4,990,340 | 2/1991 | Hidaka et al. | 424/449 |
| 5,024,671 | 6/1991 | Tu et al. | 623/1 |

FOREIGN PATENT DOCUMENTS 86903612.9 7/1987 European Pat. Off. .
WO8700046 1/1987 Japan .

OTHER PUBLICATIONS

Lindhe et al, J. Clinical Periodontology: 1979: 6: 141–149.
Goodson et al, J. Clinical Periodontology: 1979: 6: 83–92.
Dunn et al, Proceedings of the 9th Internat'l Symposium on Controlled Release of Bioactive Materials (1982):157–9.

Primary Examiner—Edward J. Webman
Attorney, Agent, or Firm—Blakely, Sokoloff, Taylor & Zafman

[57] ABSTRACT

The present invention is a timed release drug delivery system using hollow fibers. The drug contents of the voids in the fibers are delivered to the immediate environment of the fiber through the two open ends of each fiber. The present invention further includes a method of using a vacuum chamber for filling the fibers with the drugs to be delivered, and a method to control the manufacturing process of the hollow fibers containing drugs to obtain a certain rate of drug release. The present invention further includes fabrics manufactured from such drug delivery fibers, and articles made from such fabrics, such as vascular grafts and disposable surgical clothing.

12 Claims, 4 Drawing Sheets

METHOD OF MAKING A DRUG DELIVERY SYSTEM USING HOLLOW FIBERS

BACKGROUND OF THE INVENTION

The field of this invention is drug delivery systems. More specifically the field of this invention is fabrics or fibers that contain drugs or other chemicals for various purposes, and which deliver these substances outside the fabric or fiber at a later time for various purposes. Furthermore the invention includes a method for filling such chemicals into such fibers or fabrics.

In the past various drug delivery systems have been developed based on fibers that are made to contain drugs within the fiber. Under later conditions the drugs are released from the fibers and delivered to the environment around the fibers for various purposes. See for example U.S. Pat. No. 5,024,671, by Tu et al., and U.S. Pat. No. 4,801,458, by Hidaka et al. Both of these patents use porous fibers containing medication that deliver the medication rapidly through pores in the fibers. However these inventions have various drawbacks. It is difficult and expensive to make quality control checks on the porosity of the fibers, and therefore to their rate of delivery. Furthermore the consistent creation of pores in the fibers is almost impossible and sometimes requires chemical treatment of the fibers to create pores. This treatment results in severe physical degradation of the engineering properties of the fibers and makes it difficult or impossible to use the drug-bearing fiber to make a strength-bearing cloth. Therefore the fibers have to be incorporated into other strength-providing fibers in order to make fabrics. This complicates the manufacture of such items as vascular grafts and bandages.

SUMMARY OF THE INVENTION

The present invention uses hollow fibers of a material that is not necessarily porous. The contents of the fibers contained in the hollow space are delivered to the immediate environment of the fiber through the two ends of the fibers to which the interior hollow reaches.

The present invention also includes a method of using a vacuum chamber for filling the hollow fibers with the contents to be delivered. This comprises taking the original hollow fibers, with only air trapped in the hollow spaces within the fibers, and submerging the fibers in a container containing a solution of the drugs or other chemicals that are targeted to be contained in the fibers. The container with the solution of fibers is then placed in a vacuum chamber and the air pressure is reduced in the vacuum chamber. This draws out the air within the hollow within the fiber, creating a vacuum in the fiber voids. With the fibers still submerged in the solution, the air pressure is then restored inside the vacuum chamber. This causes the vacuum within the fibers to draw the liquid solution into the hollows of the fibers, replacing the vacuum with the liquid solution. The fibers can then be examined by microscopy. Fibers filled with liquid look clear without dark streaks because the refractive indexes of the fiber and the liquid are similar. However, unremoved air remaining in the hollows in the fibers appears as dark streaks because of significantly different refractive indexes of the fiber and the air.

DETAILED DESCRIPTION OF THE PREFERRED EMBODIMENTS

Figure 1:
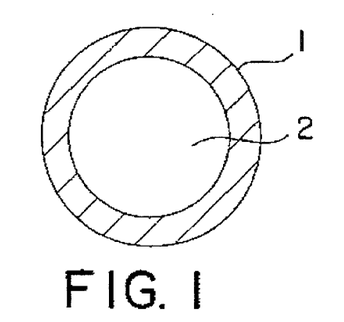
FIG. 1 shows a cross section of a typical single-hole hollow fiber.

FIG. 1 shows a cross section view of a typical single-hole hollow fiber with the fiber material 1 and the hollow space 2.

Figure 2:
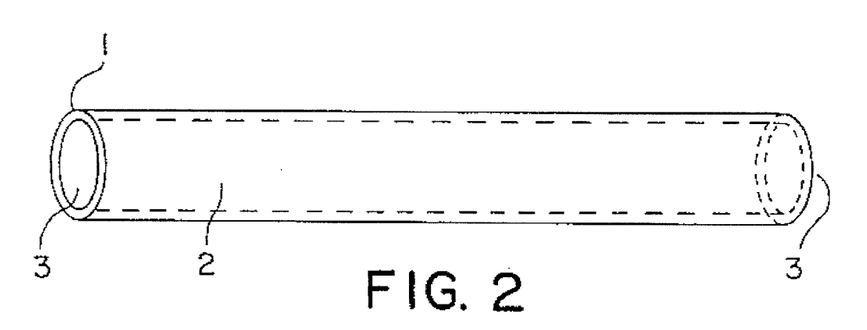
FIG. 2 shows a schematic side view of a typical single-hole hollow fiber.

FIG. 2 shows a side schematic view of a typical hollow fiber showing the fiber material 1, the hollow space 2 inside the fiber, and the end of the hollow which allows air and liquid to enter and exit through the end of the fiber 3.

Figure 3:
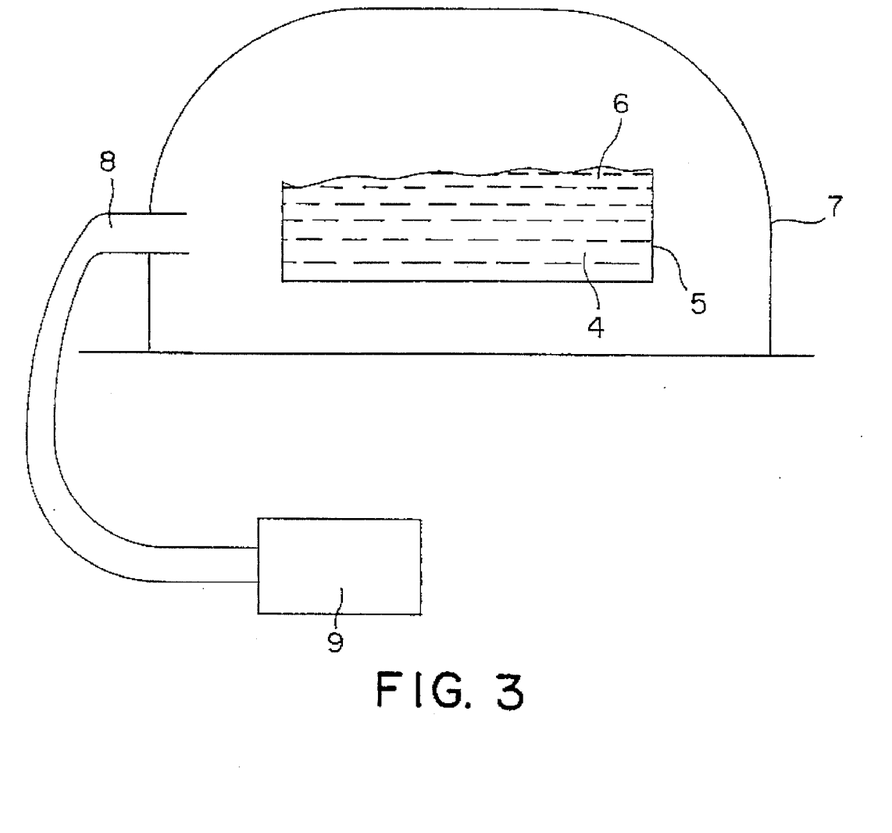
FIG. 3 shows a schematic view of the apparatus for filling the hollow fibers with a substance.

FIG. 3 shows a schematic view of the apparatus using a vacuum chamber to fill the substance into the fiber. A mass of fibers 4 is shown as hash marks. These are placed in a container 5 which holds a liquid substance 6. The container 5 with the fibers 4 and liquid substance 6 is placed within a vacuum chamber 7 which has an air exit 8 and a vacuum pump 9. When the vacuum pump 9 is operated, air is withdrawn from inside the vacuum chamber 7 creating the vacuum inside the chamber as well as inside the hollow fiber. When the control valve is loosened, air is let back into the vacuum chamber 7 allowing the air pressure there to return to normal.

Figure 4:
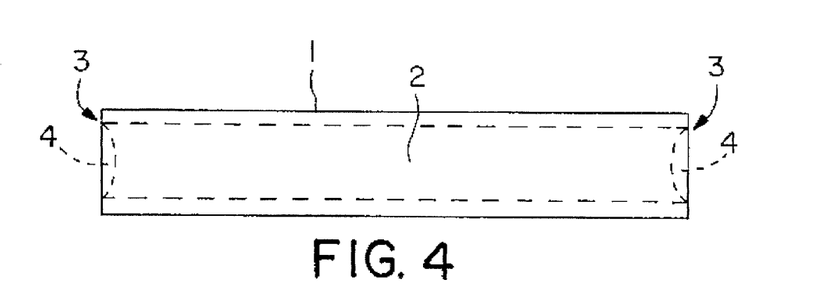
FIG. 4 shows a schematic side view of a hollow fiber submerged in a liquid but still full of air.

To fill the substance into the hollow in the fiber, the fibers 4 are placed in the container 5 and the solution 6 is added submerging the fibers. FIG. 4 shows a schematic cross sectional view of a fiber in this situation. The fiber is surrounded by a liquid solution which penetrates slightly through the ends of the fiber by capillary action.

Figure 5:
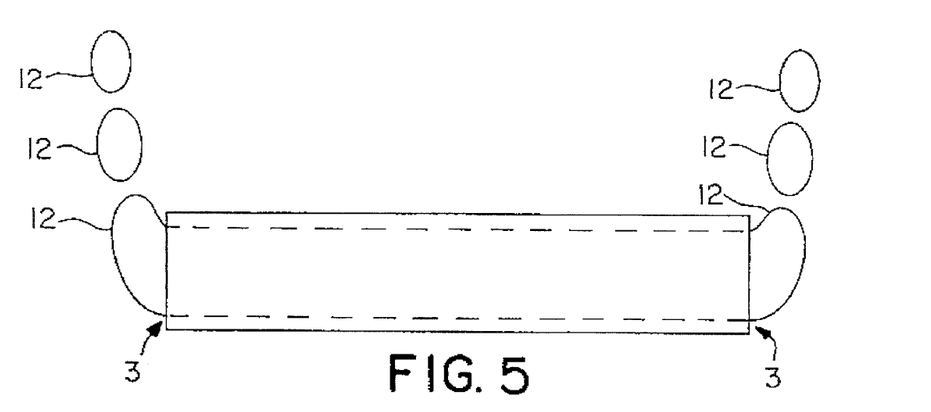
FIG. 5 shows a hollow fiber submerged in a liquid when the atmospheric pressure is being reduced, drawing the air out of the hollow.

Then most of the air in the chamber 7 is withdrawn, creating a partial vacuum in the chamber 7. This causes the air within the hollow to expand, creating a partial vacuum in the hollow fiber. The expanding air in the hollow leaves the fibers, bubbling through the liquid. FIG. 5 shows this condition with air 12 leaving the fiber through each end 3.

Figure 6:
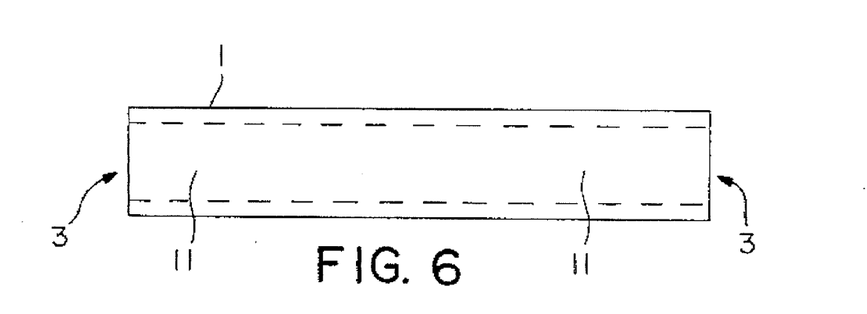
FIG. 6 shows a schematic side view of a hollow fiber after the hollow fiber void is filled with liquid.

Then the air is let back into the chamber increasing the air pressure back to normal. This causes the remaining air inside the hollow of the fiber to contract, drawing the liquid into the fiber. FIG. 6 shows a cross sectional view of the fiber in this condition. Liquid 11 has been drawn into the fiber filling the entire hollow.

The rate of delivery of the contents from the fibers is controlled by controlling the length of the fibers. That is, the rate of delivery of the contents will be approximately inversely proportional to the length of the fiber. That is, longer fibers of a certain length X will have a rate of delivery that is one half of the rate of delivery of shorter fibers with a length of one half X. This is because the shorter fibers will have twice the number of end holes per unit weight of fiber or per unit weight of contents held and to be delivered.

The rate of delivery can also be varied by changing the total cross-sectional area of the hollows. The total percentage hollow area in cross section can be altered by changing each fiber's percentage of hollowness. A higher rate of delivery can be obtained by increasing each fiber's percentage hollowness. Likewise, a lower rate of delivery can be obtained by reducing the fiber's percentage hollowness.

The rate of delivery of the contents can also be controlled by controlling the fiber size. A larger fiber will deliver the drug at a higher rate, and a smaller fiber will deliver the drug at a lower rate.

Also, the rate of delivery of the contents can be controlled by controlling the concentration of the drug. A higher drug concentration yields a higher diffusion rate. A lower concentration yields a lower diffusion rate.

The rate of delivery of the contents from the fibers may also be controlled by using a dull instrument to cut the fibers. A dull instrument rather than a sharp instrument will partially pinch the fiber in cutting it, thereby restricting the size of the end hole in the fiber.

These approaches permit the fiber to have a rate of delivery adjusted to the intended use, which is easily obtained and precisely controlled without degrading the physical quality of the material. It is relatively simple to precisely control and monitor the length to which the fibers are cut. Likewise cutting the fibers does not generally degrade the material of the fiber and therefore permits the filled fiber to be used in a woven, knitted, or felt-like matted fabric. This in turn facilitates the manufacture of articles such as vascular grafts and bandages from the impregnated material without using a mixture of other fibers for strength.

Examples of how the basic unfilled fibers may be manufactured and purchased are indicated in U.S. Pat. 3,772,137, by Tolliver. Fibers similar to those described are currently being manufactured by the DuPont Company from polyethylene terephthalate (often known as "Dacron™" when manufactured by DuPont), and by other companies from various substances.

Fibers treated in this manner may be made into fabrics, and sheets or tubes. Various drugs in solution may be filled into the hollow fibers in this manner. Basically any liquid or dissolved drug or chemical can be so filled. Examples of drugs that may be used for medical purposes include antibodies, antibiotics, anticoagulants, cardiac medication, antiviral medication, anti-AIDS medication, anti-metabolites, anti-fungal agents and steroids. Substances in slurries, suspensions, or emulsions can also be so filled into the fibers. Water repellent or fragrances may be used to fill the voids.

Tests run by the inventor have shown that this method deposits drug solutions within hollow fibers. In the tests, the fibers released the drugs slowly at rates that have been made to vary from 3 days to 2 weeks by altering the length of the fibers, the number of hollows in each fiber, and the fiber diameter.

Basic hollow fibers of this type can be made of polyethylene terephthalate, rayon, nylon, Teflon™ or cotton. Cotton is a natural fiber that is naturally hollow. Applications of such impregnated fibers and materials can be used for both medical and non-medical purposes.

Fibers and fabrics made in this manner, that are treated with antibiotics to prevent infection and to encourage healing, can be used for certain kinds of prostheses, such as vascular grafts. An artificial graft made of such material can be filled with an antibiotic to prevent post-operation infections around the surgical field, with steroids to prevent rejection of the graft material, and with antimetabolites to prevent excessive scar formation around the graft. Likewise they may be filled with heparin, an anticoagulant, to prevent excessive clotting around the prosthesis.

Other applications include filling the fibers with an antiseptic and an antifungal agent and manufacturing the material into disposable hospital sheets.

Also surgical gowns, caps and masks can be made out of material filled with antiseptic or antiviral agents (including antiviral agents effective against AIDS). Bandages can also be made out of materials treated with antiseptics to avoid infection or with growth stimulating agents to promote healing.

Furthermore, insect repellents or insecticides can be filled into materials and fabrics in this manner to make clothing that repels insects.

The present invention may also be used to deliver antifungal agents through diapers to prevent diaper rash. Such a drug used in this manner would release from the fabric only when wet, which is of course when they are most needed in this application.

Where the active ingredient to be placed in the fibers is normally a dry powder, then the ingredient must be dissolved in water, alcohol, or another solvent (or placed in a liquid in an emulsion, suspension, slurry or other form), in order to be put into the hollow fiber as discussed above.

Once the fiber is filled with the active ingredient, the fiber will usually be dried before being worked or used. This can be done by freeze-drying, convection drying, or by microwave or other heating. This will leave the dry active ingredient in the hollow of the dry fiber, which can then be worked to make the final product (which can be stored in dry form).

Then just before use, the product made from the fiber can be wetted with the appropriate liquid to restore the active ingredient to its liquid form and make it readily diffusible out of the fiber. The product also can be used dry where it will be adequately wetted after application (due to the wetness of the site of use) to allow diffusion of the active ingredient.

Active ingredients that are inherently liquids, of course, cannot be dried, and must be worked, stored and used as liquids.

The embodiments as illustrated and discussed in this specification are intended only to teach those skilled in the art the best way known to the inventor to make the invention. Nothing in the specification should be considered as limiting the scope of the present invention. Many changes could be made by those skilled in the art to produce equivalent inventions without departing from this invention. The present invention should be limited only by the following claims and their legal equivalents.

For example, any natural and artificial materials may be used to make the hollow fibers which are then filled with the agents for later delivery. Furthermore the filled fibers may be mixed and used with a variety of other fibers that are untreated or treated, to form composite materials for uses incorporating delivery of the drugs or other carried agents. Furthermore different medical and non-medical agents and chemicals not described herein may also be used for delivery by the hollow fibers described herein. Furthermore the material made from the fibers, and the fibers themselves, may be manufactured into a variety of other finished products which could then be used for other uses including the timed delivery of the agents that they contain.

Furthermore the hollow fibers can also be made of cellulose, polyacrylonitrile, acetate, rayon, polyamide (nylon), polyethylene terephthalate (polyester), cotton, polyvinyl alcohol, polyethylene, polypeptide, polypropylene, polystyrene, polyvinylchloride, or polyurethane.

In the experiments, a vacuum in the chamber was used of from $10^{-2}$ torr. to $10^{-4}$ torr., but other vacuum pressures can be used.

Any drug may be incorporated into the hollow by the present invention, and this may include hydrophilic (aqueous based), hydrophobic (oil or lipid based), or slurries (liquid in combination with solid particles).

The drugs or other contents may be released from the hollows within the fibers by diffusion, vaporization, capillary action, liquid flow, liquid leakage, or other means. Where the drug or other contents are eventually found in the hollow in solid form (either by incorporation in a slurry, the liquid portion of which later evaporates, leaving the solid drug particles behind, or by incorporation in a solution, where the liquid later evaporates, leaving the dissolved drugs to come out of the solution as a solid), then the solid drugs may leave the hollow fiber by redissolving when in contact with new liquids and moving out by diffusion, capillary action, or a liquid flow.

Fabrics made out of the treated materials as described herein may be knitted, woven, or non-woven fabrics.

Medical sheets and gowns are currently often made by non-woven polyethylene terephthalate fibers which are chopped and then pressed. They may be bonded or mechanically-entangled or otherwise formed into fabric in a method similar to manufactured paper. Articles that may be made out of materials treated in this manner may include also disposable shoe covers for the surgical theater. Furthermore, a non-woven material may be used to make products such as diapers, sheets, masks, gowns, surgical caps, shoe covers and bandages.

Knitted or woven fabrics may be used for the manufacture of vascular grafts, other prosthetic grafts, sutures, pillows, disposable tarps, disposable clothes or nets, or other materials.

Fragrances or sleep-inducing drugs may also be incorporated in the materials to be released as vapors.

The present invention may also be incorporated into artificial insulating fabrics such as Thinsulate™, to make insulated disposable clothes or nets filled with chemicals. These chemicals can include insect repellent to be used in sporting or outdoor environments. Likewise, mildew resistant chemicals or drugs could be used for such outdoor applications. Furthermore, rain gear may be made of hollow fiber, fabrics treated in this matter to contain water-repellant materials. This may yield a fabric that is both water repellant but can "breathe", that is, it can pass air and water vapor between the weave of the fabric.

Note that hollow polyethylene terephthalate fibers are hydrophobic and normally do not wet well. However, these fibers can be made hydrophilic (i.e., easily wettable) by treating them with a basic solution. For example, hollow polyethylene terephthalate fibers can be treated with a basic solution such as sodium hydroxide and ethanol, and then rinsed with distilled water, to make them hydrophilic.

For convenience in explanation, embodiments are shown and described in this specification with fibers with one axial hollow. However, a fiber with multiple parallel axial hollows within each length of fiber can equally as well embody this invention. For example, fibers are currently made and can be used in the present invention that have one, four and seven hollows, respectively, running for the length of the fiber.

Figure 7:
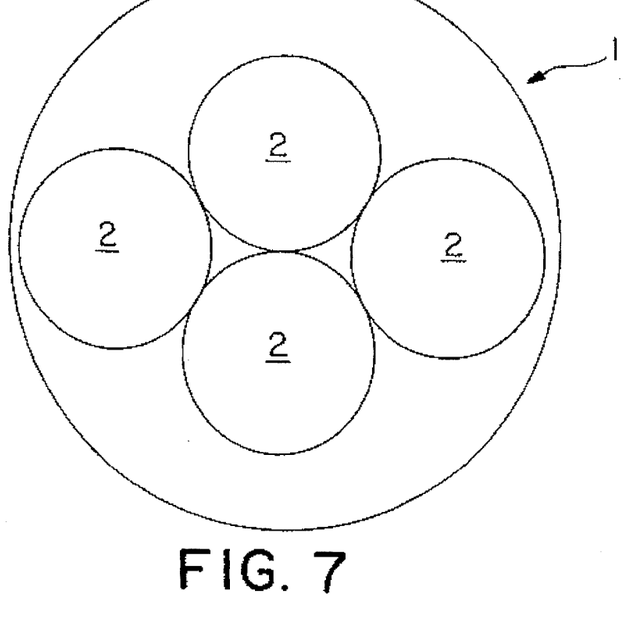
FIG. 7 shows a cross section of a typical four-hole hollow fiber.
Figure 8:
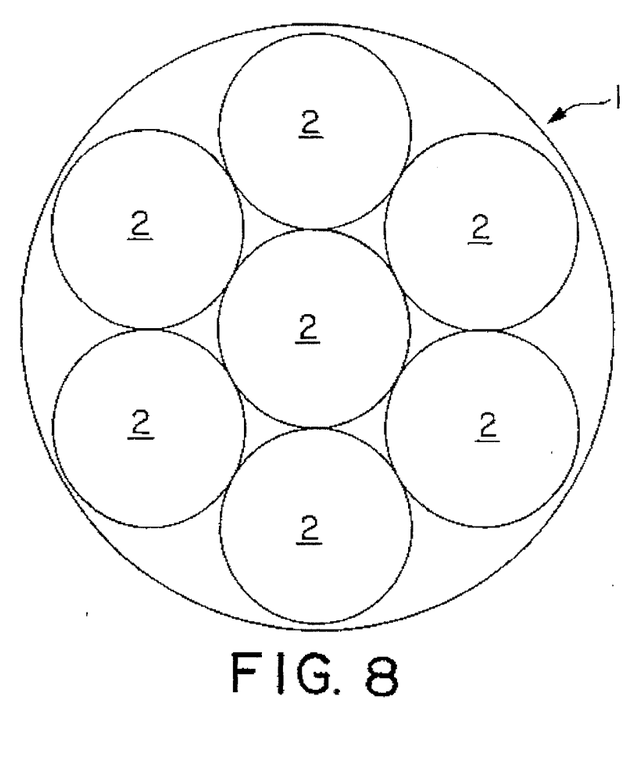
FIG. 8 shows a cross section of a typical seven-hole fiber.

FIG. 7 shows a cross section view of a four-hole hollow fiber with the fiber material 1 and the four hollow spaces 2. FIG. 8 shows a cross section view of a seven-hole hollow fiber with the fiber material 1 and the seven hollow spaces 2.

Experimental Results

The inventor undertook experiments using the present invention, and the results are indicated in Tables I, II and III.

Table 1 describes the results of preparation of commercially available hollow Dacron™ (polyethylene terephthalate made by DuPont) fiber, 1.3 denier per filament T-727W (single-hole with 15% void), with vacuum-filling of the hollow fibers with salt solution, and testing the filled fiber for controlled time release of the salt solution. A 4.0 gram sample of 3.81 centimeters cut length was prepared by cutting the fiber with a sharp razor. The fiber diameter was 11.56 microns and the void diameter was 4.49 microns. (The sample could also have been prepared by cutting a large rope band, e.g. 1,000,000 denier, with a Lummus cutter.) The fiber had tenacity of 4.5 grams per denier and elongation of 24.0% It is important to cut the hollow fiber with sharp blades to keep fiber voids fully open (see FIG. 2).

The sample was placed in a capetri dish and carefully pushed down with a small metal plate weighing approximately 20 grams to keep the sample down in the dish during vacuum operation (see FIG. 3). A 30.0% salt solution was poured into the dish until the fiber sample was completely submerged in the solution. After the sample dish was placed. On a vacuum chamber, the vacuum pump (a Fisher Scientific Precision Direct-Drive Pump Model DD-90) was turned on for five minutes to obtain a vacuum of at least $1.0 \times 10^{-2}$ torr. Numerous air bubbles are observed escaping from the fiber sample at this time. (It is desirable that the air in the fiber voids be completely removed and a vacuum created.) Then the vacuum pump was turned off and the vacuum chamber was rapidly returned to atmospheric pressure. This caused the vacuum in the fiber voids to be replaced with salt solution. All fibers were completely filled with salt solution in five minutes. These solution-filled fibers looked clear under an optical microscope while the air-filled fibers have dark streaks along the voids because of refractive index differences.

The filled fibers were then washed thoroughly with distilled water to remove all salt solutions from the surface of fibers. Then the fibers were submerged in 200 ml. of distilled water. The amount of salt solute diffused into the distilled water from the filled fibers was measured by a Fisher Scientific conductivity meter (Cat. No. 09 325 360, Range 0–19,990 micromhos), since the amount of sodium chloride ions in the distilled water is directly proportional to the conductivity of the current in the solution. The salt was diffused out of the fibers rapidly during the first day and thereafter the salt diffusion rate gradually slowed down. Upon completion of the test, the fibers still maintained their original tensile properties, i.e., tenacity of 4.5 grams per denier and elongation of 24.0%.

Table I also shows the results of the preparation of hollow commercially available Dacron™ polyester fiber, 5.5 denier per filament T-334W (single-hole with 15% void), with vacuum-filling of the hollow fibers with salt solution, and testing for the controlled time release of the salt solution. A 4.0 gram sample of 3.81 centimeters cut length was prepared by cutting the fibers with a sharp razor. The fiber diameter was 23.75 microns and the void diameter was 9.20 microns. The fiber had tenacity of 3.8 grams per denier and elongation of 36.0%. The fibers were vacuum-filled with salt solution as described above. The diffusion rate of 5.5 denier per filament of fiber was more rapid than that for 1.3 denier per filament. The vacuum-filling and diffusion test did not affect tensile properties of the fibers.

Table I also illustrates the results of the preparation of 4-hole hollow Dacron™ polyester fiber, 5.5 denier per filament T-808 (4-hole with 15% void). A 4.0 gram sample of 3.81 centimeters cut length was prepared by cutting the fibers with a sharp razor. The fiber had tenacity of 3.5 grams per denier and elongation of 37.0%. The sample was subsequently prepared and tested as described above. Its diffusion rate was slower than that for 5.5 denier per filament T-334W.

Table II demonstrates the results of filling knit fabric produced from Dacron™ fiber, 1.3 denier per filament, 3.81 centimeters cut length, T-727W hollow fibers, with a saturated salt solution, and then testing for controlled time release of the salt solution.

A fiber sample with a tow denier of 1,000,000 denier was commercially cut on a tow carousel cutter manufactured by Lummus Industries (of Columbus, Ga.) to produce fibers with 3.81 centimeters cut length. Using conventional cotton textile system processing equipment from carding, drawing, and roving to spinning, yarns with 10 to 1 and 20 to 1 cotton counts were produced. These yarns were then knit into a sample fabric on a commercial knitting machine for testing. A 4.0 gram fabric sample was cut with a sharp razor and filled with 30.0% salt solution as described for Table I. After rinsing the fabric sample thoroughly with distilled water to remove salt solution from the surface of the fabric, the sample was submerged in 400 ml. of distilled water to test for the diffusion rate of salt from the fiber voids into the water. The diffusion rate behavior was identical to that of 1.3 denier per filament fiber, demonstrating that yarn making and fabric knitting processes did not deform the fibers or alter their drug delivery properties.

Table II also shows filling of knit fabric produced from 5.5 denier per filament, 3.81 centimeters cut length T-334W hollow fibers, with 30% salt solution, and testing for the controlled time release of the salt solution. A fiber sample with a rope denier of 1,000,000 denier was commercially cut on a Lummus cutter to produce fibers from 3.81 centimeters cut length. Using conventional cotton textile system processing equipment from carding, drafting, and roving to spinning, yarns with 10 to 1 and 20 to 1 cotton counts were produced. A 4.0 gram fabric sample was prepared and vacuum-tested as shown in Table II. The diffusion rate was very similar to those examples in Table I, indicating that yarn and fabric making processes did not affect the fiber voids.

Application to Specific Drugs

Heparin

Table III demonstrates the preparation of 1-hole hollow Dacron™ polyester fiber, 1.3 denier per filament T-727W, and Dacron™ fiber 5.5 denier per filament T-334W and its knit fabric, with vacuum-filling of the hollow fibers and knit fabric with heparin (an anticoagulant) and testing for the controlled time release of heparin.

Using commercially available 1-hole hollow Dacron™ polyester fibers, 1.3 denier per filament T-727W, and 5.5 denier per filament T-334W and its knit fabric, a 4.0 gram sample for each item was prepared for testing as described above for Table I. Each sample was vacuum-filled with heparin at a concentration of 40,000 units per 150 cc. The diffusion rate was rapid initially and was gradual later, similar to the samples with saturated salt solutions.

Aristocort

Aristocort (a steroid) at a concentration of 320 mg/15 cc was filled into hollow fiber in a fashion similar to the heparin described above. The diffusion rate behavior was similar to that of heparin.

Cefazolin

Cefazolin (an antibiotic) at a concentration of 4 mg/75 cc was filled into hollow fibers in a manner similar to the heparin described above. The diffusion rate was very low from the beginning, unlike the above solutions.

From the information in Table 1, one can conclude that hollow fibers having different deniers and different numbers of holes can be easily filled with solutions of various substrates which later diffuse out of the hollow fibers in the presence of a solvent or distilled water. Sodium chloride effectively diffused out of 1.3 dpf (denier per filament) fine fibers as well as the larger 5.5 dpf fibers.

The following conclusions are drawn from the information in Table II.

1) Knit fabric samples produced from the hollow fibers essentially maintained the diffusion rates of the non-knit fiber samples, indicating that the fabric making process did not affect each fiber's void.

2) Coarse fabric samples produced from coarse yarns (10 to 1 cotton count) and softer fabric samples produced from finer yarns (20 to 1 cotton count) had about the same diffusion rate. Thus, fabric samples having different textures or aesthetics can be produced for different applications without affecting diffusion rates.

The following conclusions are drawn from the information in Table III.

1) All drugs filled easily into hollow fibers and effectively diffused out of hollow fibers or knit fabrics produced from hollow fibers.

2) Drugs diffused out of knit fabrics as effectively as from hollow fibers.

3) Cefazolin (an antibiotic) had a higher diffusion rate than Aristocort and a more sustained drug release than heparin. This pattern is ideally suited for clinical applications since antibiotics are better applied clinically when applied locally in high concentrations for a prolonged time. Heparin, however, is needed only for a short period of time to prevent early thrombosis, and steroids are used in small concentrations for a prolonged time.

Diffusion Rate

The diffusion rate of the present invention is equal to the amount of the solute diffused out of the hollow fiber, divided by the total cross-section area of the hollow fiber voids. This is illustrated in the following formula:

$$\text{Diffusion Rate} = \frac{\text{Amount of solute diffused out of hollow fiber}}{\text{(total cross-section area of hollow fiber voids)}}$$

The diffusion rate is measured in units of grams per square centimeter.

The diffusion rate is proportional to the percentage of the fiber cross-section that is hollow divided by the length of the fiber. This is illustrated by the formula.

$$\text{Diffusion Rate} \propto \frac{\text{Hollow cross-section \%}}{\text{length of fiber}}$$

TABLE I

| Example | Sample Type | Denier per filament/ fiber cut length (dpf/cm) | Total Area of Open Void (4.0 gm sample) (sq. cm) | Type of solution in Fiber Void (in distilled water) | Diffusion Rate (grams/hr) After 2 hours | Diffusion Rate (grams/hr) After 12 hours |
|---|---|---|---|---|---|---|
| 1 | 1.3-T-727W 1-hole fiber | 1.3/3.81 | 0.230 | NaCl (30 gm/100 cc) | $1.20 \times 10^{-2}$ | $6.25 \times 10^{-4}$ |
| 2 | 1.3-T-727W 1-hole fiber | 1.3/10.16 | 0.086 | NaCl (30 gm/100 cc) | $5.99 \times 10^{-3}$ | $4.44 \times 10^{-4}$ |
| 3 | 5.5-T-334 1-hole fiber | 5.5/3.81 | 0.114 | NaCl (30 gm/100 cc) | $8.40 \times 10^{-3}$ | $2.94 \times 10^{-3}$ |
| 4 | 5.5-T-334 1-hole fiber | 5.5/10.16 | 0.043 | NaCl (30 gm/100 cc) | $4.60 \times 10^{-3}$ | $1.08 \times 10^{-3}$ |
| 5 | 5.5-T-808 4-hole fiber | 5.5/3.81 | 0.114 | NaCl (30 gm/100 cc) | $1.052 \times 10^{-2}$ | $2.10 \times 10^{-3}$ |
| 6 | 5.5-T-808 4-hole fiber | 5.5/10.16 | 0.043 | NaCl (30 gm/100 cc) | $9.13 \times 10^{-3}$ | $9.41 \times 10^{-4}$ |

TABLE II

| Example | Sample Type | Denier per filament/ fiber cut length (dpf/cm) | Total Area of Open Void (4.0 gm sample) (sq. cm) | Type of solution in Fiber Void (in distilled water) | Diffusion Rate (grams/hr) After 2 hours | Diffusion Rate (grams/hr) After 12 hours |
|---|---|---|---|---|---|---|
| 1 | 1.3-T-727W 20/1 yarn Knit fabric | 1.3/3.81 | 0.230 | NaCl (30 gm/100 cc) | $1.07 \times 10^{-2}$ | $4.50 \times 10^{-4}$ |
| 2 | 5.5-T-334W 20/1 yarn Knit fabric | 5.5/3.81 | 0.114 | NaCl (30 gm/100 cc) | $1.00 \times 10^{-2}$ | $8.80 \times 10^{-4}$ |
| 3 | 5.5-T-334W 10/1 yarn Knit fabric | 5.5/3.81 | 0.114 | NaCl (30 gm/100 cc) | $9.36 \times 10^{-3}$ | $9.00 \times 10^{-4}$ |

TABLE III

| Example | Sample Type | Denier per filament/ fiber cut length (dpf/cm) | Total Area of Open Void (4.0 gm sample) (sq. cm) | Type of solution in Fiber Void (in distilled water) | Diffusion Rate (grams/hr) After 2 hours | Diffusion Rate (grams/hr) After 12 hours |
|---|---|---|---|---|---|---|
| 1 | 1.3-T-727W 1-hole fiber | 1.3/3.81 | 0.230 | Cefazolin (4 gm/150 cc) | $1.12 \times 10^{-2}$ | $7.80 \times 10^{-4}$ |
| 2 | 5.5-T-334 1-hole fiber | 5.5/3.81 | 0.114 | Cefazolin 4 gm/150 cc) | $1.56 \times 10^{-3}$ | $1.87 \times 10^{-4}$ |
| 3 | 5.5-T-334 Knit fabric | 5.5/3.81 | 0.114 | Cefazolin (4 gm/150 cc) | $8.19 \times 10^{-4}$ | $1.03 \times 10^{-4}$ |
| 4 | 1.3-T-727W 1-hole fiber | 1.3/3.81 | 0.23 | Aristocort (320 mg/150 cc) | $6.00 \times 10^{-5}$ | $2.57 \times 10^{-5}$ |
| 5 | 5.5-T-334 1-hole fiber | 5.5/3.81 | 0.114 | Aristocort (320 mg/150 cc) | $4.20 \times 10^{-5}$ | $1.83 \times 10^{-5}$ |
| 6 | 5.5-T-334 Knit fabric | 5.5/3.81 | 0.114 | Aristocort (320 mg/150 cc) | $3.75 \times 10^{-5}$ | $1.11 \times 10^{-5}$ |
| 7 | 1.3-T-727W 1-hole fiber | 1.3/3.81 | 0.230 | Heparin (40,000 units/150 cc) | 189 (units/hr) | 3.4 (units/hr) |
| 8 | 5.5-T-334 1-hole fiber | 5.5/3.81 | 0.114 | Heparin (40,000 units/150 cc) | 72 (units/hr) | 8 (units/hr) |
| 9 | 5.5-T-334 Knit fabric | 5.5/3.81 | 0.114 | Heparin (40,000 units/150 cc) | 54 (units/hr) | 5.7 (units/hr) |

I claim:

1. A method of making an active agent delivery system comprising:

(a) providing an elongated, substantially non-porous, hollow fiber having at least one interior void open at each end of the fiber;

(b) cutting the ends of the fiber to make a plurality of fibers, (c) submerging the cut fibers in a liquid containing an active agent, (d placing the submerged fibers in a vacuum chamber, (e) drawing air out of the void by withdrawing the air the air in the vacuum chamber, and (f) drawing the liquid containing the active agent into the void by allowing the air pressure in the vacuum chamber to return to the ambient pressure.

2. The invention in claim 1, further comprising:

(a) drying the liquid from the fiber, leaving the substance dry in the voids of the fiber.

3. The method of claim 1, where the fibers are made of one member selected from the group consisting of polyester, rayon, cotton, cellulose, polyacrylonitrile, polyvinyl alcohol, polyamide, polyethylene, polypeptide, polypropylene, polystyrene, polyvinylchloride, polyurethane.

4. The invention in claim 1, where the active agent is one member selected from the group consisting of medical drugs, insect repellent, water repellent, and fragrances.

5. The method of claim 4 wherein said medical drugs are selected from the group consisting of antibodies, antibiotics, cardiac medication, anti-viral agents, anti-AIDS medication, anti-metabolites, and steroids.

6. The method of claim 5 wherein said antibiotics comprise antiseptics.

7. The method of claim 6 wherein said antibiotics comprise anti-fungal agents.

8. The method of claim 5 wherein said cardiac medication is an anticoagulant.

9. The method of claim 1 wherein the air pressure in the vacuum chamber is reduced to a pressure in the range of $10^{-2}$ to $10^{-4}$ torr.

10. The method of claim 1 wherein said active agent is in a liquid selected from a hydrophilic and a hydrophobic material.

11. The method of claim 1 wherein said active agent is in a slurry, suspension or emulsion.

12. The method of claim 1, where the fibers are made of polyethylene terephthalate.

* * * * *

UNITED STATES PATENT AND TRADEMARK OFFICE
CERTIFICATE OF CORRECTION

PATENT NO. : 5,538,735
DATED : July 23, 1996
INVENTOR(S) : Ahn

It is certified that error appears in the above-identified patent and that said Letters Patent is hereby corrected as shown below:

In column 6 at line 23, please delete " capetri " and insert -- Petri --.

In column 6 at line 28, please delete " placed. " and insert -- placed in a vacuum chamber, the vacuum pump --.

In column 6 at line 29, please delete " On a vacuum chamber, the vacuum pump "

In column 6 at line 59, column 7 at line 12, 37,56, and 61, please delete " T-334W " and insert -- T-334 --.

Signed and Sealed this

Tenth Day of March, 1998

*Attest:*

BRUCE LEHMAN

*Attesting Officer*     Commissioner of Patents and Trademarks